United States Patent [19]

Celanza

[11] 4,219,329
[45] Aug. 26, 1980

[54] DENTAL CAST RELATOR

[76] Inventor: Frank V. Celanza, 30 Wenwood Dr., Brookville, N.Y.

[21] Appl. No.: 33,004

[22] Filed: Apr. 24, 1979

Related U.S. Application Data

[63] Continuation-in-part of Ser. No. 886,420, Mar. 14, 1978, abandoned.

[51] Int. Cl.³ ............................................ A61C 11/00
[52] U.S. Cl. ...................................................... 433/58
[58] Field of Search ......................... 433/63, 54, 58, 57

[56] References Cited

U.S. PATENT DOCUMENTS

| 2,600,899 | 6/1952 | McClain | 433/63 |
| 3,059,336 | 10/1962 | Windish | 433/54 |
| 3,409,986 | 11/1968 | Freeman | 433/56 |

*Primary Examiner*—Robert Peshock
*Attorney, Agent, or Firm*—Jacobs & Jacobs

[57] ABSTRACT

The present invention relates to a device for use in dentistry as an aid to the production of very accurate dental restorations such as inlays, crowns, bridges and the like. In its essentials the invention provides an instrument having two parallel plate members, spaced apart, wherein the top plate preferably has one straight edge at the rear thereof and a forwardly projecting area to which a stone model may be secured. The lower plate is rectangular and is adapted to have secured thereto a stone model of the patient's mating jaw, the plates being mounted for relative vertical movement to bring the opposed teeth of the two jaws into the patient's functional bite position. The upper and lower plates are supported vertically and in spaced parallel relation by two posts disposed laterally of the central protruding portion of the top plate and on either side of the stone jaw reproductions. The posts slide within outer upper cylinders secured to the top plate.

14 Claims, 9 Drawing Figures

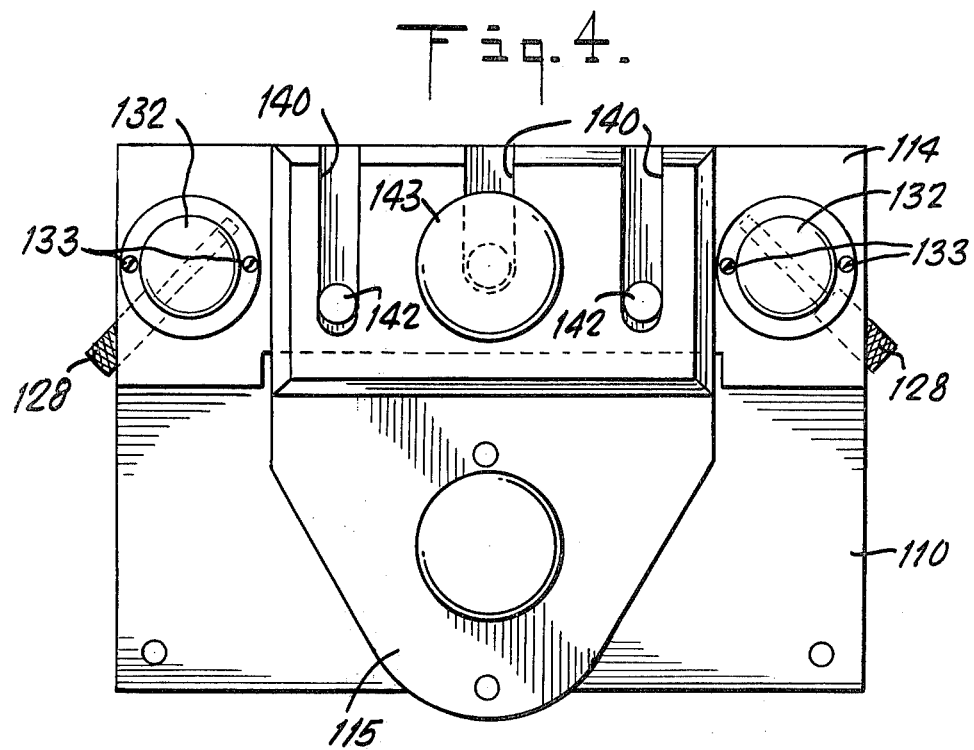
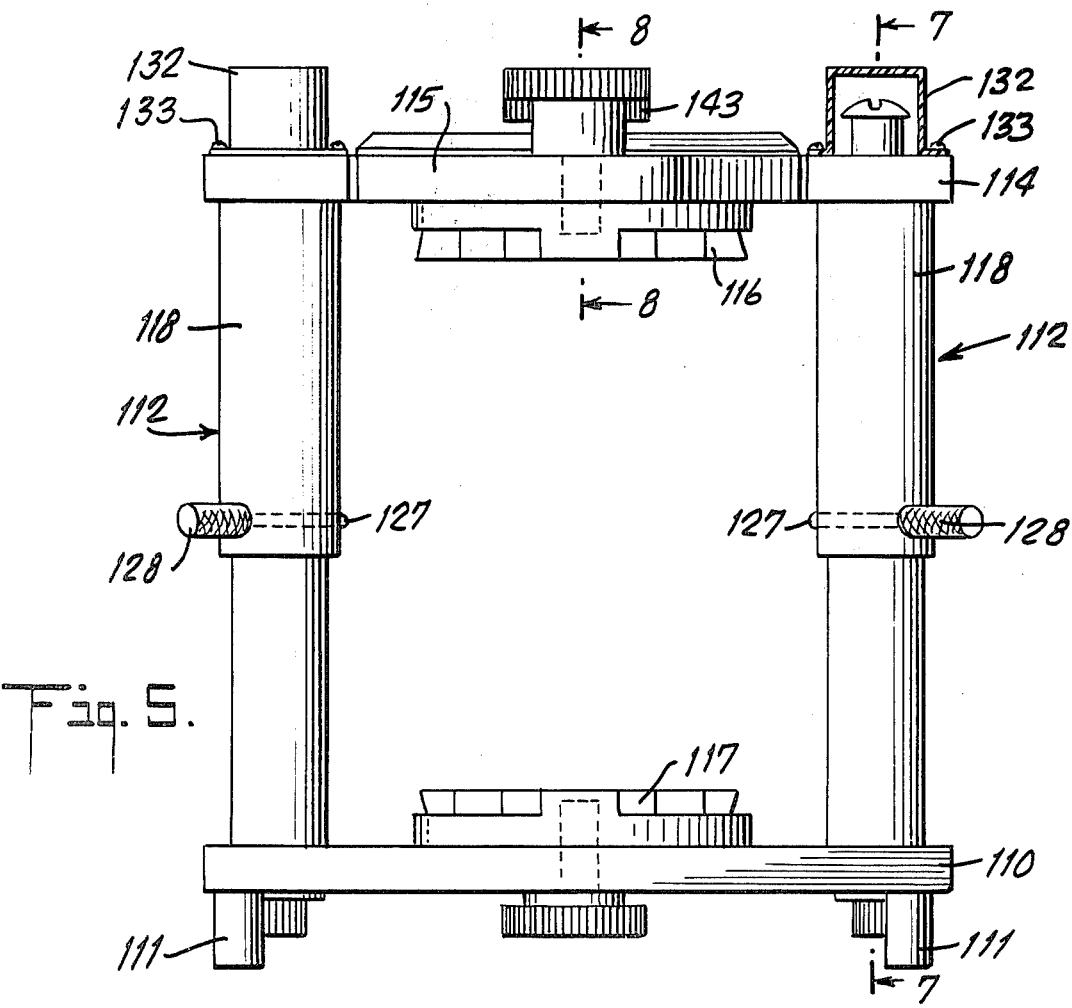

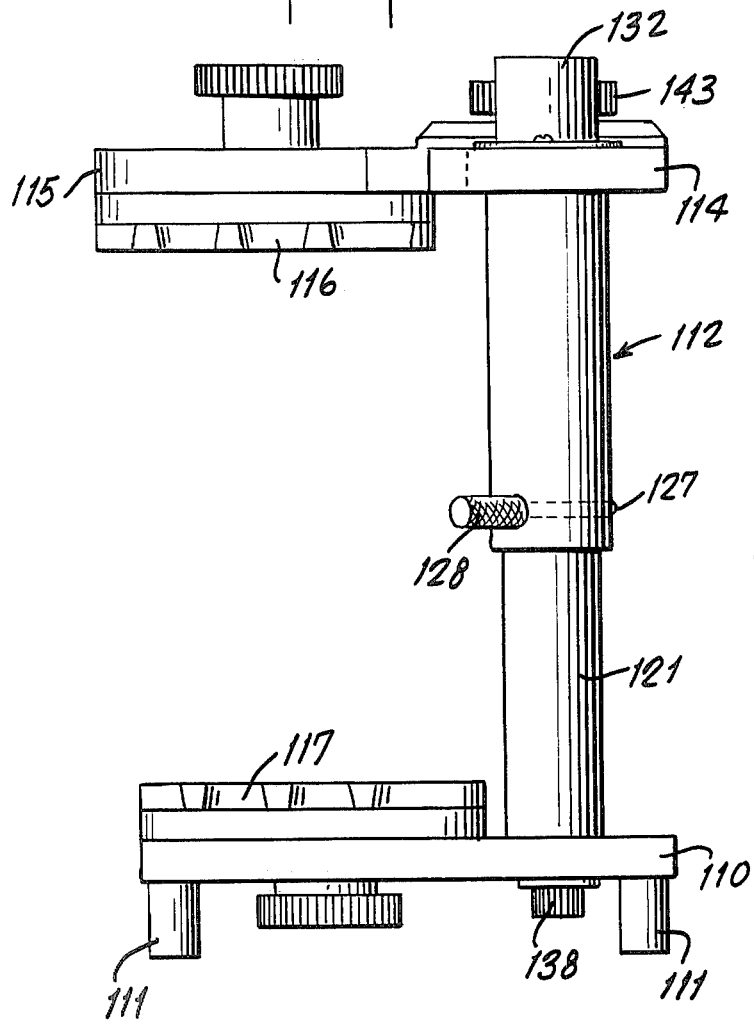
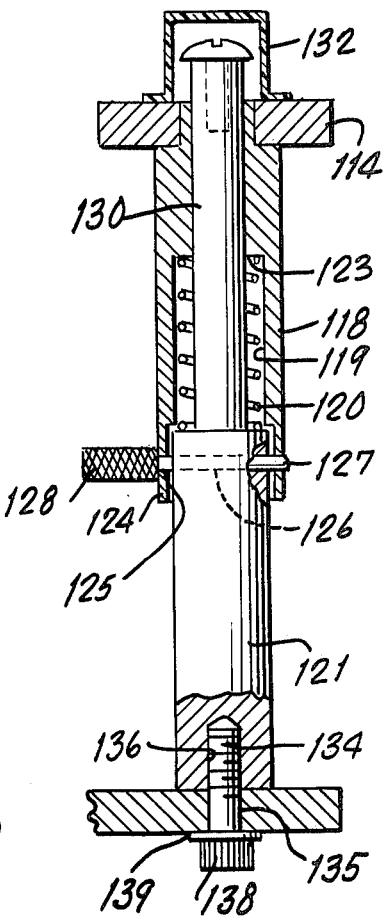
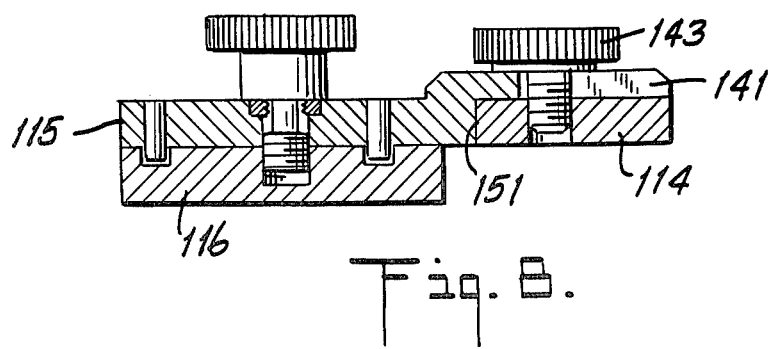

DENTAL CAST RELATOR

This application is a continuation-in-part of my copending application Ser. No. 886,420, filed Mar. 14, 1978 and now abandoned.

The present invention relates to a device for use in dentistry as an aid to the production of very accurate dental restorations such as inlays, crowns, bridges and the like. More particularly, it provides what the inventor prefers to call a dental cast relator, wherein the patient's functional bite is reproduced prior to the preparation of the dental restoration, and then the restored teeth in the form of wax inlays, crowns and bridges are formed to provide such restoration in a form closely approximating the final metallic restoration so as to provide proper functional bite without interference between the jaw to which the restoration is applied and the mating jaw with which it cooperates.

The device of the present invention permits the dentist to perform most of the work of forming the restoration in finished metal away from or outside of the patient's mouth, so that in finished form when installed in the patient's mouth it requires very little if any final grinding or sizing to blend into and form part of the patient's functional bite.

In its essentials the invention provides an instrument having two parallel plate members, spaced apart, wherein the top plate preferably has one straight edge at the rear thereof and a forwardly projecting area to which a stone model may be secured. The lower plate preferably is rectangular and is also adapted to have secured thereto a stone model of the patient's mating jaw,—the plates being mounted for relative vertical movement to bring the opposed teeth of the two jaws into the patient's functional bite position. The upper and lower plates are supported vertically and in spaced parallel relation by two posts disposed laterally of the central protruding portion of the top plate and on either side of the stone jaw reproductions. The posts slide within outer upper cylinders secured to the top plate.

Among the features of the present invention are:

(a) intermediate the length of each post there is a shoulder which is precision machined and which serves as a stop to prevent over-closure of the upper and lower stone models;

(b) a heavy duty coil spring surrounds a reduced portion of each post and engages the lower end of a cylinder and the upper end of the precision stop;

(c) separate removable mounting plates are provided for the upper and lower stone models for attachment to the inner surfaces of the top and bottom plates of the device;

(d) the vertical posts which serve as guides during the opening and closing movements of the stone models are balanced and not cantilevered so that any tendency of the stone models to cant when hand pressure is applied to the upper plate of the device is eliminated;

(e) the instrument is designed to handle both full and quadrant models;

(f) the instrument is leveled on both sides by carefully machined protruding feet so that it can be readily inverted for ease in mounting the stone models; and (g) centric pins are provided which lock the stone mounting plates in proper position on the upper and lower plates of the instrument so that upon removal and later replacement the stone models will always assume the same positions. These pins are also used to confirm the level of the occlusal position after the restorations have been adjusted. The pins will not seat if the adjustments are not complete.

The instrument can be used with any crown and bridge technique. It also can be used in duplicating or relining dentures,—the centric pins serving to lock the denture in place and to prevent any change in vertical and loss of the centric position during curing.

BACKGROUND OF THE INVENTION

Dental alignment holders for use in producing dental restorations are well known in the art. The prime function and purpose of such dental alignment holder is to produce dental restorations which conform to the functional bite of the patient. Such dental alignment holders are used in the preparation of inlays, crowns, bridges, and the like.

The customary technique followed in utilizing such dental alignment holders is to prepare two stone models of the patient's jaws and to mount such models on such dental alignment holders. The technique for preparing such stone models may be summarized as follows: a functional bite is chewed in by the dental patient to provide a static record of the dynamic action of the mastication movements of the jaws. This static record of the functional bite of the patient is obtained by the dentist by placing softened dental wax over the prepared teeth and the masticating action of the opposed teeth with respect to the prepared teeth are recorded in wax. From this impression a dynamic record of the functional movements of the opposed teeth is poured in stone and a static functional counter cast or dental functional cast is formed which contains all of the movements of mastication such as centric, working lateral, balancing lateral, protrusive, etc. An impression of the prepared teeth is also taken for making a dental working cast which may contain removable dies which represent the prepared tooth or teeth which are to receive the dental restorations.

One prior art device which is sold under the trademark "Verticulator" is generally shown and described in U.S. Pat. No. 3,059,336, dated Oct. 23, 1962, in the name of August W. Windish, and assigned to J. F. Jelenko & Co., Inc. This instrument has two cantilever arms, each of which is supported in a horizontal direction by a heavy metal block with the two blocks normally spaced from each other by coil springs and guiding pins. The stone models are mounted on the inner faces of the cantilever arms so that when the supporting blocks are pushed downwardly into engagement with their cooperating or mating surfaces the teeth on the stone models are brought into functional bite position. It will first be recognized that the broad flat surfaces of the mating blocks must be extremely carefully machined, otherwise any irregularities on the mating surfaces of the blocks will be magnified by the cantilever arms and transmitted to the dental restorations. Also, the vertical pins which engage in the two blocks to guide the same in a vertical direction must have very close tolerances with the mating holes in each block to prevent canting of the blocks and hence magnification of error in the stone models. Such close tolerances frequently give rise to binding when hand pressure is applied to the surface of the upper block to press it into engagement with the lower block. Also, as far as is presently known, such cantilever types of instruments are not adapted for application with both quadrant and full denture models. Thus it is customary in the dental field to have two such instruments,—one for use with quadrants and the other for use with full denture models.

Applicant is also familiar with the following U.S. patents:

| Number | Dated |
| --- | --- |
| 613,772 | Nov. 8, 1898 |
| 1,027,443 | May 28, 1912 |
| 1,033,562 | July 23, 1912 |
| 1,684,393 | Sep. 18, 1928 |
| 2,611,961 | Sep. 30, 1952 |
| 3,067,515 | Dec. 11, 1962 |

None of these prior art patents discloses the salutary features of the present invention, nor do they disclose the universality of the instrument of the present invention.

THE PRESENT INVENTION

The present invention provides an instrument especially useful in dentistry as an aid to the production of very accurate dental restorations such as inlays, crowns, bridges, and the like, which in final form very closely reproduces the natural functional bite of the patient without interference between the jaw to which the restoration is applied and the mating jaw with which it cooperates. Some of the advantages and characteristics of the present invention are summarized above and identified as (a) through (g). Other advantages and distinctions over the prior art will be made more apparent from the following detailed description.

For a better understanding of the invention reference will now be made to the accompanying drawings wherein.

These three figures were shown in application Ser. No. 886,420, filed Mar. 14, 1978, of which this application is a continuation-in-part.

An improved modification of the earlier invention is now shown in FIGS. 4 to 9, inclusive, wherein:

FIG. 4 is a top plan view of the improved cast relator of the present invention.

FIG. 5 is a front elevational view of the improved dental cast relator of the present invention with certain parts being broken away to show underlying structure.

FIG. 6 is a side elevational view of the improved cast relator shown in FIG. 5.

FIG. 7 is a sectional view taken along the line 7—7 of FIG. 5 and viewed in the direction of the arrows.

FIG. 8 is a sectional view taken along the line 8—8 of FIG. 5 and viewed in the direction of the arrows.

Figure 9:
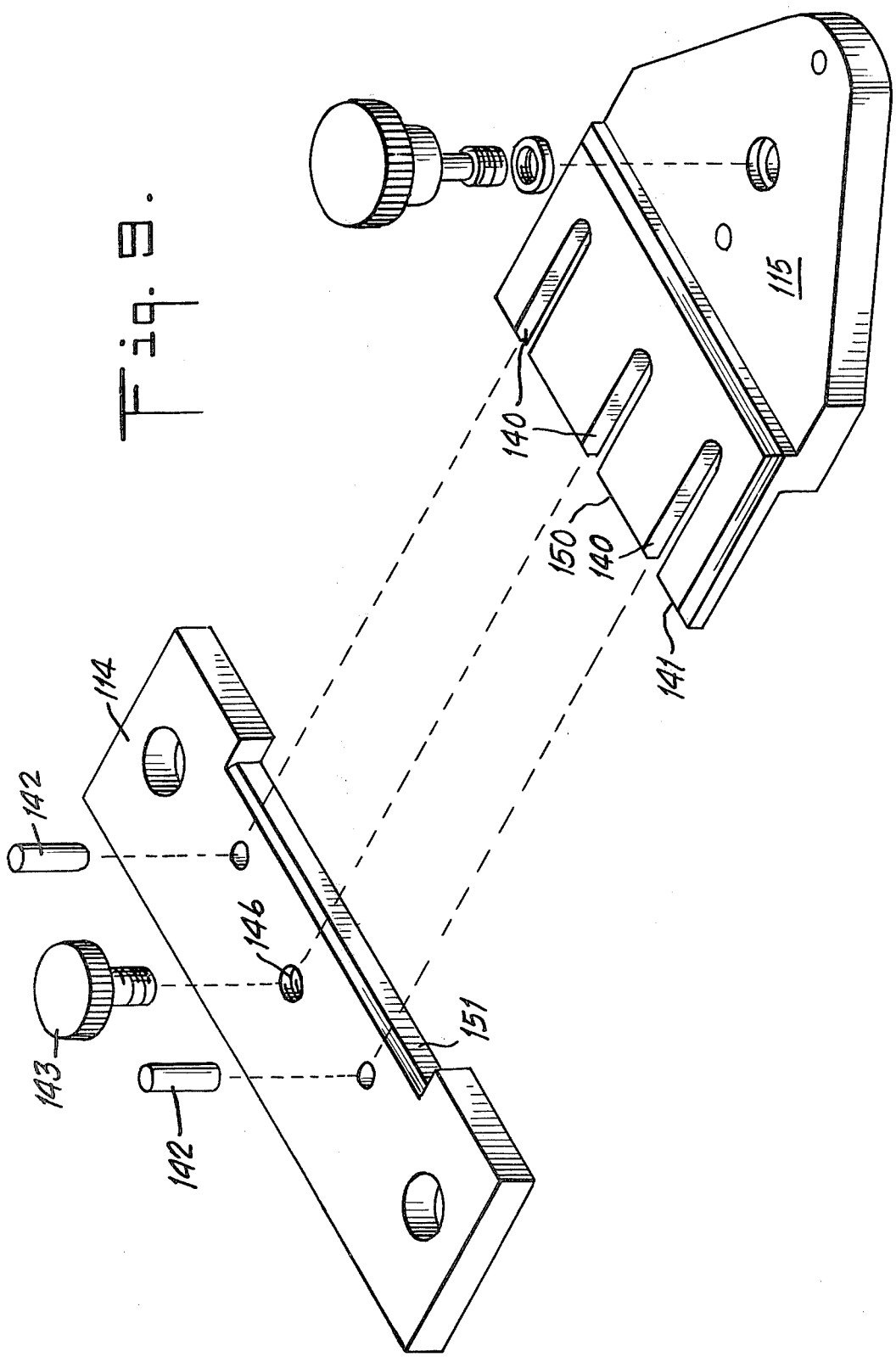

FIG. 9 is an exploded view in perspective, of the improved upper mounting plate of the present invention and its associated parts.

Figure 1:
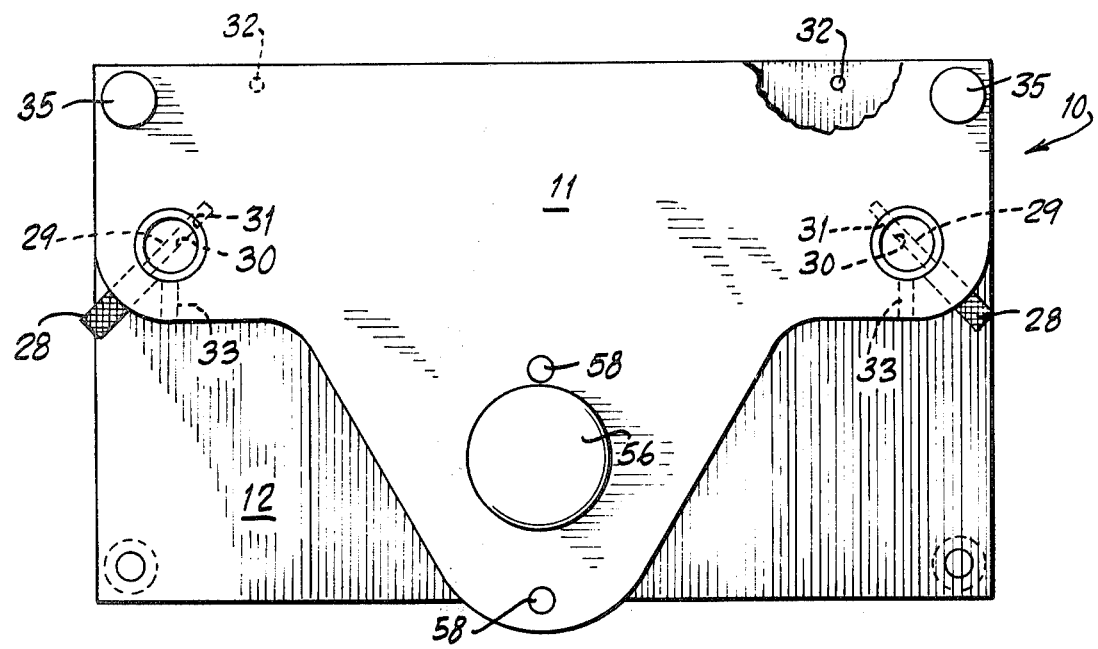
FIG. 1 is a top plan view of the dental cast relator provided by the present invention.
Figure 2:
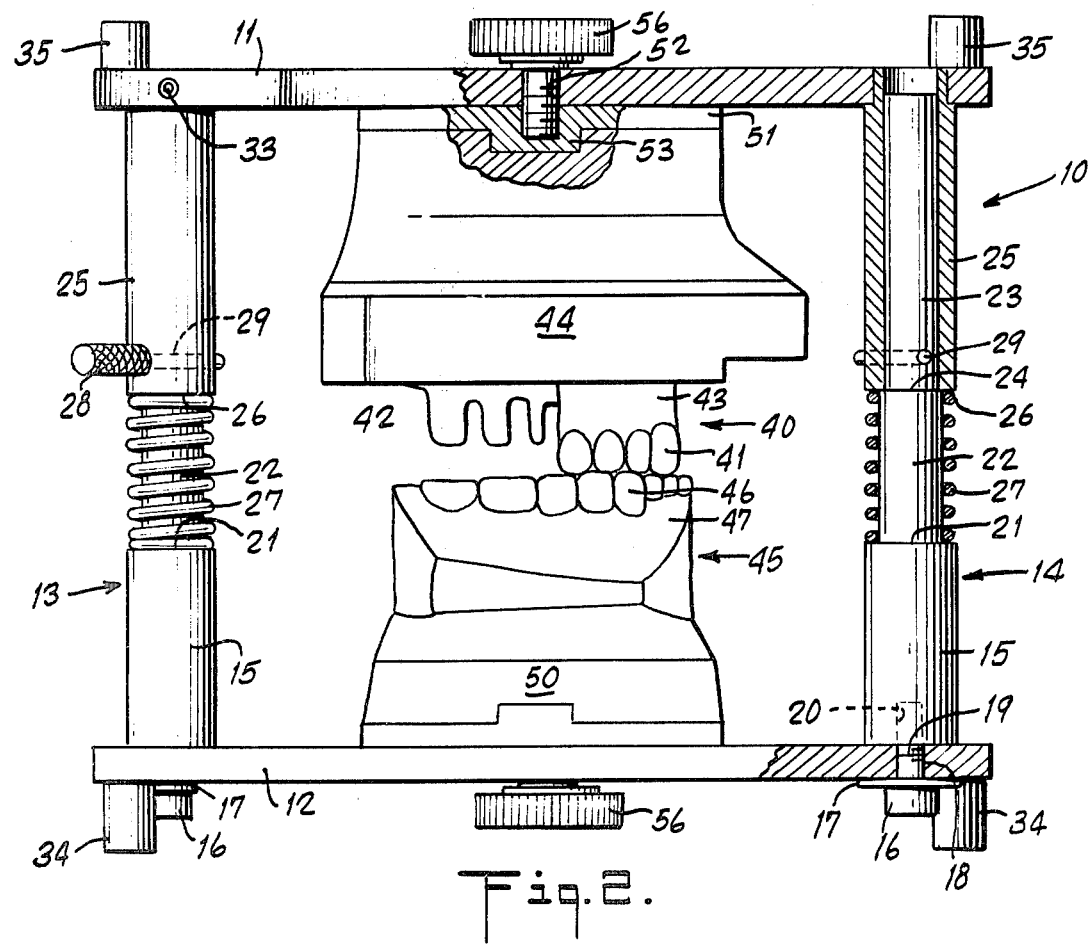
FIG. 2 is a front elevational view of the dental cast relator of the present invention with certain parts being broken away to show underlying structure.
Figure 3:
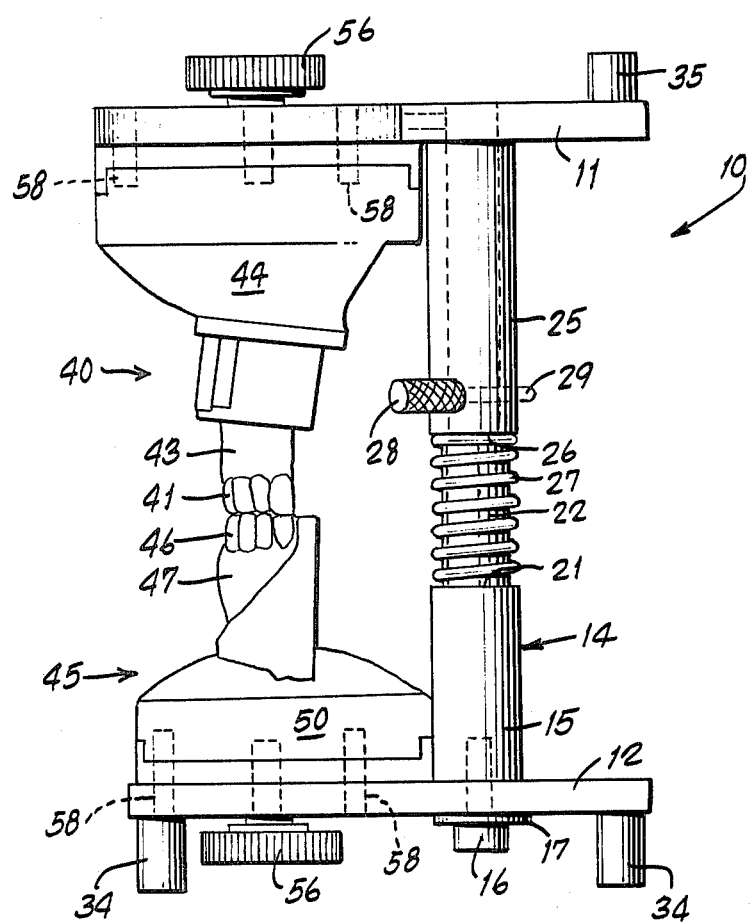
FIG. 3 is a side elevational view of the device of the present invention as shown in FIG. 2.

Referring now first to FIGS. 1 to 3, inclusive, of the drawings for a more detailed description of the invention as shown therein, 10 generally refers to the device which consists of a top plate 11 and a bottom plate 12 which are arranged to be parallel to each other and spaced apart in such parallel relationship by two side posts 13 and 14 secured to the plates 11 and 12 and holding them in spaced parallel relationship as best seen in FIG. 2. The lower end 15 of each post is of cylindrical form and is secured to the bottom plate 12 by a bolt 16, a washer 17, a hole 18 in the plate and a screw-threaded portion 19 which is threaded into a screw-threaded hole 20 in the lower end of the cylindrical bottom member 15 of the post. At its upper end the lower end 15 of each post has a shoulder 21 which is formed by an intermediate reduced portion 22 of the post. The upper end 23 of the reduced portion 22 is further reduced in diameter to provide a shoulder 24 which is precision machined so that its upper engaging surface is very accurately located and defined. A sleeve 25 snugly engages the upper reduced end of the post 23 with its lower end 26 having a precision machined shoulder engaging the shoulder 24 so that relative movement between the top plate and bottom plate in a downward vertical direction is limited by the engagement of shoulder 26 on sleeve 25 with shoulder 24 on the intermediate section. An expansion coil spring 27 surrounds the intermediate section 22 and engages shoulders 21 and 26.

As best seen in FIG. 1 pins 28 having enlarged knurled heads for ease in manual manipulation have reduced shanks 29 which are adapted to be manually inserted at an angle of approximately 45° into matching holes 30, 31 in the sleeve 25 and the upper reduced end 23 of post 14 so as to hold them in assembled relation against the action of expansion coil spring 27. The top of each sleeve 25 is secured to the top plate by set screws 33.

It will be understood that when the pins 28 are manually removed from the matching holes 30, 31 in the sleeve 25 and upper end 23 of the post, the spring 27 is free to expand and to urge the top plate upwardly. For convenience, storage holes 32 are provided in bottom plate 12 for storing the pins 28 when not in use.

It will also be noted that the bottom plate is provided with four legs 34 one at each corner of the plate which are machine ground and dimensioned to stand firmly and in parallel on top of a laboratory table or work bench. Similar legs 35 are provided on the top plate and protrude upwardly therefrom. Thus, it will be understood that in use the device may be turned upside down on a laboratory work bench or other flat surface and the device will be maintained in a predetermined horizontal position.

In FIGS. 2 and 3 an upper working cast 40 of stone material which in the present instance is shown as a quadrant of the patient's upper jaw shows natural teeth 41 and prepared tooth stubs 42 ready to receive caps or crowns separately or as part of a multiple-toothed dental restoration. The gum structure is shown at 43. This upper working cast 40 is suitably supported in a plaster holder 44. The functional lower cast is shown at 45 and includes natural teeth 46 and gum structure 47. The lower functional cast 45 is also imbedded in and mounted on a plaster support 50. The upper surface of the plaster support 44 is removably secured to member 51, preferably of polystyrene. A screw-threaded hole 52 extends through the top plate 11 and into a boss 53 provided on the under surface of the plaster support member 50—the boss having a screw-threaded hole therein. A knurled thumb screw 56 is screwed into the hole 52 in the plate 11 and into the hole in the boss 50 and thereby retains the entire upper working cast and its associated parts in secure engagement with the under surface of top plate 11. Also, as can be seen in FIGS. 1 and 3, alignment pins 58 are disposed outwardly of the thumb screw 56 and along the median line of the upper plate 11 such pins being disposed in holes formed in the upper plate 11 and the plaster support member 50. In this way the upper working cast is properly located on the under surface of the plate 11 and can be removed and replaced whenever necessary without any change in relative position.

A similar mounting assembly is provided for the functional cast 45 by parts bearing identical reference numerals. Thus as shown in FIGS. 2 and 3, the quadrant of the upper jaw having teeth requiring caps, crowns, bridgework, or the like are mounted in functional bite position with the teeth of the lower functional cast when the device is in the position as shown in these figures and the pins 45 are in place in the matching holes 30, 31.

In the use of the device of the present invention the previously prepared tooth stubs 42 are suitably waxed with tooth shapes in the form of caps, crowns, or bridgework to assume the shape and bite of the finished restoration. In doing the waxing the upper plaster holder 44 may be moved out of bite engagement by the removal of pins 28 which will permit the coil springs 27 to expand and to urge the cylinders 25 and upper plate 11 upwardly. In final testing of the wax-up the upper plate 11 should be pressed downwardly manually against the action of the coil springs so as to bring the upper reproduction and lower reproduction into normal bite engagement, and the pins 28 reinserted in holes 30, 31 to hold them in the position shown in FIGS. 2 and 3. When the wax-up is deemed to be accurate and finished, the wax-up is removed from the stone model and is suitably cast in metal by conventional dental casting methods utilizing centrifugal casting apparatus in accordance with the well known lost wax process.

After the burrs and sprues are removed from the castings and they are ground and polished, the metal castings of the restorations are then ready for trial testing on the stone model by insertion over the prepared tooth stubs 42. When thus applied to the tooth stubs the upper plate 11 is manually moved upwardly and downwardly to bring the restorations and reproductions of adjacent natural teeth into normal bite engagement with the reproduction of the lower jaw natural teeth until it is determined that the restorations conform with and complete the natural bite of the patient. This condition is finally determined when it is possible to reinsert the pins 28 into the holes 30, 31 of the device.

Suitable porcelain facings may then be applied to the labial surfaces of the cast restorations for aesthetic purposes.

It will be understood that with the present invention the posts 13, 14 are disposed on opposite sides of the mating stone models and equidistant therefrom so that on manually raising and lowering the upper plate against the action of the coil springs 27 there is no canting of one stone model with respect to the other. Furthermore, because the shoulders 24 and 26 are precision-ground and precisely located on the posts 13, 14, there is no possibility of error introduced into the biting effect by an error in alignment of such shoulders with respect to the stone models when in functional bite position.

It will be also understood that with the mounting provided by the present invention for both the upper and lower stone models on mounting plates 51, merely by loosening the thumb screws 56 it is possible to remove the entire stone assembly including mounting plates 51 from the device for work away from the same and to reinstall them in the original positions with the help of the alignment pins 58, 58 and reinsertion of the thumb screws 56. This feature also permits the same device to be used concurrently in the preparation of other restorations, including restorations on full reproductions. It is also possible to use the device for relieving various areas of a denture or for relining the same.

It will be well recognized and understood that the mounting plates and attached casts may be removed from one dental cast relator and replaced on another without error. This results from the precision machining, which allows the dentist to retain his instrument and send the mountings to the laboratory for fabrication of the restorations without error.

As before pointed out, the device may be upended from the position shown in FIG. 2 to a position where the teeth to be restored are in the lower stone model if this should be of advantage in working on the same. It is thus believed that the present device overcomes most, if not all, of the disadvantages of prior art devices and possesses a universality which is not found in any prior art device.

Reference will now be made to FIGS. 4 to 9, inclusive, which show an improved embodiment of the present invention.

In FIGS. 4 to 9, inclusive, the device consists essentially of a bottom plate 110 of substantially rectangular shape, having supporting legs 111 at each of its corners for supporting the device on a dental laboratory bench or table.

Rearwardly of the front edge of the base plate and at each side thereof, there is provided a vertically extending cylindrical post 112 of a dimension and construction later to be described.

At the upper end of each post 112 there is a top plate member 114 suitably secured to such posts and having a forward projecting area 115 which overlaps, is parallel to, and is spaced from the comparable area of the bottom plate 110.

The top plate 114 is provided with a denture casting attaching member 116 (preferably of polystyrene), which is complementally located vertically with respect to a similar denture casting attaching member 117 on the bottom plate 110. The positioning of the denture casting attaching members 116 and 117 is at a precise vertical distance so that they can be transferred from one instrument (constructed according to the present invention) to another identical instrument without loss of precision. In further explanation of this it should be again emphasized that the dental cast relator of the present invention is designed and constructed to be a precise instrument so that there is no room for error in reproducing the natural bite of the patient and in testing for the natural bite on any instrument constructed in accordance with the present invention.

As earlier explained, stone working casts or models are prepared in prosthetic restorative work of both the upper jaw and the lower jaw of the patient, with such stone working casts showing the patient's missing teeth or the teeth to be restored by caps, inlays, bridges and the like. When such stone working casts have been prepared, the upper jaw cast is secured to the upper denture casting attachment member 116 by intervening plaster, and the lower jaw working cast is also secured to the lower jaw dental casting attachment member 117 by plaster. When such upper and lower stone working models are thus assembled on the device and the device is in the condition shown in the drawings, the teeth of such stone models will be in the natural bite position of the patient except for the restorative work which has to be done.

With the preciseness of the instrument of the present invention it is possible for the dentist who designed the dental restoration by utilizing the device of the present invention to retain such instrument in his own office and only send the mounting plates, plaster retention members and stone working cast to the dental laboratory. The dental laboratory, in turn, is only concerned with reproducing in metal the wax dental restoration as designed by the dentist. Hence, the dental laboratory which does similar work for other dentists may be equipped with a plurality of identical instruments and may interchange the denture casting attachment members 116, 117 with any equally precise instrument constructed according to the present invention merely by attaching them to the upper and lower plates 115 and 110.

It will be noted by referring to FIGS. 5, 6 and 7 that each of the posts 112 has an outer sleeve 118 having an internal axial bore 119 which houses a compression spring 120. The post 112 also has a lower plunger or piston type member 121 which engages within such outer sleeve and internal bore so that the compression spring 120 engages the upper surface 122 of the piston 121 and the upper end 123 of the bore 119.

There is also provided in both posts 112, in the overlapping sleeve extension 124 and in the piston member 121, respectively, through holes 125, 126 for accommodating pins 127 which are inserted into such through holes to retain the sleeve 118 and piston 121 in the exact position shown in the drawings. For convenience each pin 127 has a knurled head 128 for facilitating hand insertion and removal.

An important feature of the present invention is that the pins 127 and the through holes 125, 126 are precision machined to coincide precisely with the level of the shoulder stop which, in turn, defines the exact bite of the patient. With the pins in place the instrument is locked during the mounting procedure in all three planes, thus preventing any change in dimension and position during the setting of the mounting material.

It will be understood that when the pins 127 are removed the sleeve 118 may be moved upwardly and downwardly against the action of compression spring 120, relatively to the piston 121. Thus, merely by pressing down on the upper plate 114 the upper stone model and the lower stone model may be pressed into and out of biting contact. When the restoration has been completed and the bite level is correct, the pins 127 may be reinserted in the through holes 125, 126. If reinsertable, the correct bite level is confirmed and no more revisions of the restoration are necessary. If the pins are not reinsertable, the restoration must be further revised until such pins can be readily inserted.

It will thus be noted that in this embodiment of the invention as contrasted with the embodiment shown in FIGS. 1 and 2, the compression spring 120 is fully enclosed within the bore of sleeve 118 which thereby prevents accumulation of dust on such spring and the sliding parts. This is important in dental laboratory work for the reason that the stone working cast or model of the upper jaw and the lower jaw is made of a refractory material which in handling can cause dust to be given off in the immediately surrounding area. Also, the plaster mountings can give off dust.

Another feature of the present embodiment is that an elongated member 130 of reduced diameter which is secured to the piston 121 and which is axially disposed within the compression spring 120 has at its upper end a plastic cap 132 which also serves to seal the upper end of the post 112 against the admission of dust. The plastic cap 132 is fastened to the upper plate by screws 133.

As best seen in FIG. 7, the lower end of each post 112 is secured to the bottom plate 110 by machine screws 134 which protrude through holes 135 in such bottom plate and are in threaded engagement with screw threaded holes 136 in the base of the piston 121,—the machine screws 134 having knurled heads 138 for easy hand removal and a washer 139 between each such knurled head and the bottom plate.

Another feature of the improved embodiment is best illustrated in FIG. 9 of the drawings wherein it will be noted that the forward projection area 115 of the upper plate 114 has an upward offset portion 115a, which in turn is removably secured to such upper plate by slots 140 which are open ended at their rearward end 141 and which are engaged by upstanding pins 142 of a size and dimension to fit snugly in such slots. Such offset portion 115a is also secured to the plate 114 by a thumb screw 142 having an enlarged head 143, said thumb screw engaging in an open ended slot 144 in the offset portion of extension member 115 intermediate the slots 140, and also engaging in a screw hole 146 in the upper plate. Thus the forward projecting area 115 which includes the denture casting attaching member 116 can be removed from the device and sent to a laboratory for completion of the restorations required without having to send along the entire instrument. Furthermore, the forward projection area 115 with its upward offset portion 115a, having attached to its underface the stone model, can be removed from time to time by a dentist for access in working and for viewing the restoration during its fabrication. It also can be used for duplicate mountings.

For the foregoing purposes it is essential, however, that the back edge 150 of the offset extension member be precision machined to mate exactly with the recessed front edge 151 of the top plate 114 so as to assure no inaccuracies in bite mating when extension member with stone model is mounted on a duplicate instrument at the dental laboratory.

It is also an essential feature of the present embodiment that the holes 125, 126 in the sleeve 118 and piston 121 be precision machined and exactly located and that the pins 127 also be precision machined in each such device so as to avoid any error as between duplicate devices and to eliminate any play between the sleeve, piston and pins. The importance of this is that in the use of the device the prosthetic dentist using the stone models of the upper and lower jaws (suitably mounted and in bite position) can by wax and other familiar techniques design the restorations required for reproduction in the dental laboratory. Then, when the restorations have been prepared, the accuracy of such restorations can be tested by the dentist merely by moving the upper plate and the lower plate by hand pressure upwardly and downwardly against the action of coil spring 120 without pins 127 being in place so as to take initial readings and observations on the bite. When it is possible to reinsert the pins 127 into the holes 125, 126, the bite will be exactly right to meet the patient's most exacting requirements.

From the foregoing it will be understood that in the practice of prosthetic dentistry the device of the present invention provides a means whereby restorative dental work such as crowns, inlays, bridges and the like can be exactly delineated from the standpoint of the natural bite and other tooth configurations of the patient; and that when the restorations have been prepared by the dental laboratory it is possible to check them on the device before having them finalized and ready for application to the patient's mouth. The device also allows duplicate mountings to be made which is further confirmation of the precision and refinement of the prostheses.

What I claim is:

1. A dental cast relator for use in the production of dental restorations, comprising a pair of plates in substantially parallel position, a pair of posts connecting said plates and separating the same in such parallel position, said plates adapted to receive and retain on their inner faces dental reproductions of a patient's upper and lower jaws and to hold them in natural bite position, one of said posts mounted on each side of said dental mounting plates, said posts being laterally spaced equidistant from said plates, each said post having three sections of varying diameters, one such section being firmly attached to one parallel plate and having a shoulder at its upper end, an intermediate section of reduced diameter surrounded by a coil spring, and an upper section of still further reduced diameter providing with said intermediate section a shoulder which is precision machined, and a cylinder surrounding said upper section and having its lower end engaging the opposite end of said coil spring, said cylinders at their upper ends secured to the other plate, said plates adapted to be moved manually to bring said upper and lower dental reproductions into natural bite engagement.

2. A dental cast relator according to claim 1, wherein the shoulders on the upper ends of the intermediate sections of the posts are so located that when in abutting relation with the cylinders they define the natural bite position of the dental reproductions.

3. A dental cast relator according to claim 1, wherein the shoulders on the upper ends of the intermediate sections of the posts are precision machined and are so located that when in abutting relation they accurately define and limit the natural bite position of the dental reproductions.

4. A dental cast relator according to claim 1, wherein holding means are provided for holding the upper and lower plates in natural bite position.

5. A dental cast relator according to claim 1, wherein holes are provided in the cylinders and the upper post sections which are aligned when the reproductions are in natural bite position and may be retained in such position by pins inserted therein.

6. A dental cast relator according to claim 1, wherein the reproductions of a patient's upper and lower jaws are supported in plaster holders which in turn are secured to mounting plates, said mounting plates being removably secured to the inner surfaces of the upper and lower parallel plates of the device by thumb screws and alignment pins.

7. A dental cast relator according to claim 1, wherein the reproductions of a patient's upper and lower jaws are supported in plaster holders which in turn are secured to mounting plates, said mounting plates being removably secured to the inner surfaces of the upper and lower parallel plates of the device by thumb screws, and being held in proper position by a pair of alignment pins which engage in coinciding holes in each said parallel plate, mounting plate and plaster holder.

8. A dental cast relator for use in the production of dental restorations, comprising a pair of plates in substantially parallel position, a pair of posts connecting said plates and separating the same in such parallel position, said plates adapted to receive and retain on their inner faces dental reproductions of a patient's upper and lower jaws and to hold them in natural bite position, one of said posts mounted on each side of said dental mounting plates, said posts being laterally spaced equidistant from said plates, each said post having three sections, one such section being firmly attached to one parallel plate and having a shoulder at its upper end, a second section of reduced diameter surrounded by a coil spring, and a cylinder section having a shoulder engaging the opposite end of said coil spring, said cylinders at their upper ends secured to the other plate, said plates adapted to be moved manually to bring said upper and lower dental reproductions into natural bite engagement.

9. A dental cast relator according to claim 8, wherein said cylinder sections fully encompass and enclose the coil springs.

10. A dental cast relator according to claim 8, wherein said cylinder sections fully encompass and enclose the coil springs and have extensions below the coil spring which overlap the first section, coinciding holes provided in such extensions and in the first sections, and a pair of pins which engage in such coinciding holes to hold said plates in normal bite position.

11. A dental cast relator according to claim 8, wherein at least one of said plates is formed in two sections adapted for locking engagement with each other, one such section constituting the front section for receiving and retaining one of the dental reproductions, the other said section constituting the rear section having laterally spaced holes therein for receiving and retaining ends of the posts, the rear section having along its forward edge an accurately machined cut-out, said front section on its underface and rearwardly of the dental reproduction mounting area having an accurately machined edge for mating engagement in said cut-out, whereby said dental reproductions are accurately positioned in normal bite position when said front and rear sections are held in locking engagement.

12. A dental cast relator according to claim 11, wherein said forward section has an upwardly offset portion at its back end with at least three open-ended slots therein, and said rear section has at least three holes therein for receiving pins and the like for engagement in said slots.

13. A dental cast relator according to claim 11, wherein said forward section has an upwardly offset portion at its back end with at least three open-ended slots therein, and said rear section has at least three holes therein for receiving pins and the like, the center hole being screwthreaded and adapted to receive a thumb screw which secures the rear portion and front portion of the plate together and also secures the dental reproduction and associated parts in normal bite relation to the other plate and dental reproduction.

14. A dental cast relator according to claim 9, wherein a cap encloses the upper end of each post and is secured to the upper plate above said cylinder, whereby dust and the like is excluded from the post sections.

* * * * *

UNITED STATES PATENT AND TRADEMARK OFFICE
CERTIFICATE OF CORRECTION

PATENT NO. : 4,219,329

DATED : August 26, 1980

INVENTOR(S) : FRANK V. CELENZA

It is certified that error appears in the above—identified patent and that said Letters Patent are hereby corrected as shown below:

ABSTRACT PAGE

Top of page, line below "United States Patent [19]", change "Celanza" to -- Celenza --; line marked "[76]", change "Celanza" to -- Celenza --

Signed and Sealed this

Twenty-first Day of April 1981

[SEAL]

Attest:

RENE D. TEGTMEYER

Attesting Officer    Acting Commissioner of Patents and Trademarks